United States Patent
Springob et al.

(10) Patent No.: US 12,383,481 B2
(45) Date of Patent: Aug. 12, 2025

(54) SILICON FREE HAIR CONDITIONING COMPOSITION

(71) Applicant: WELLA INTERNATIONAL OPERATIONS SWITZERLAND SÀRL, Petit-Lancy (CH)

(72) Inventors: Christian Springob, Lorsch (DE); Antonio Martinez-Campoy, Rüsselsheim (DE); Marion Stuess, Griesheim (DE)

(73) Assignee: WELLA INTERNATIONAL OPERATIONS SWITZERLAND SARL, Petit-Lancy (CH)

( * ) Notice: Subject to any disclaimer, the term of this patent is extended or adjusted under 35 U.S.C. 154(b) by 139 days.

(21) Appl. No.: 17/283,216

(22) PCT Filed: Oct. 30, 2019

(86) PCT No.: PCT/EP2019/079707
§ 371 (c)(1),
(2) Date: Apr. 6, 2021

(87) PCT Pub. No.: WO2020/089319
PCT Pub. Date: May 7, 2020

(65) Prior Publication Data
US 2021/0378930 A1    Dec. 9, 2021

Related U.S. Application Data

(60) Provisional application No. 62/757,821, filed on Nov. 9, 2018, provisional application No. 62/754,092, filed on Nov. 1, 2018.

(51) Int. Cl.
*A61K 8/41* (2006.01)
*A61K 8/34* (2006.01)
*A61K 8/365* (2006.01)
*A61K 8/37* (2006.01)
*A61K 8/73* (2006.01)
*A61Q 5/00* (2006.01)
*A61Q 5/12* (2006.01)

(52) U.S. Cl.
CPC .............. *A61K 8/416* (2013.01); *A61K 8/34* (2013.01); *A61K 8/342* (2013.01); *A61K 8/365* (2013.01); *A61K 8/37* (2013.01); *A61K 8/732* (2013.01); *A61Q 5/006* (2013.01); *A61Q 5/12* (2013.01); *A61K 2800/34* (2013.01); *A61K 2800/5426* (2013.01)

(58) Field of Classification Search
CPC ........ A61K 8/416; A61K 8/731; A61K 8/732; A61K 2800/5426; A61K 8/34; A61K 8/342; A61K 8/365; A61K 8/37; A61K 2800/34; A61K 8/42; A61Q 5/006; A61Q 5/12
See application file for complete search history.

(56) References Cited

U.S. PATENT DOCUMENTS

| | | | |
|---|---|---|---|
| 2006/0024256 A1* | 2/2006 | Wells ................. | A61K 8/891 424/70.13 |
| 2016/0175209 A1* | 6/2016 | Walker ................ | A61Q 5/12 424/70.28 |
| 2017/0290755 A1* | 10/2017 | Soh .................... | A61K 8/368 |
| 2018/0243198 A1* | 8/2018 | Decarlo .............. | A61Q 5/06 |
| 2018/0280270 A1* | 10/2018 | Rughani ............. | A61K 8/416 |

FOREIGN PATENT DOCUMENTS

| | | | | |
|---|---|---|---|---|
| CA | 2322853 A | | 9/1999 | |
| CN | 105560076 A | * | 5/2016 | |
| JP | 2002507547 A | | 3/2002 | |
| JP | 2008127337 A | | 6/2008 | |
| JP | 2013189423 A | | 9/2013 | |
| JP | 2015124173 A | | 7/2015 | |
| JP | 2015127314 A | | 7/2015 | |
| JP | 2016044133 A | | 4/2016 | |
| WO | WO-2013081018 A1 | * | 6/2013 | ............ A45D 7/06 |
| WO | 2014069388 A1 | | 5/2014 | |
| WO | 2018098542 A1 | | 6/2018 | |

OTHER PUBLICATIONS

Chelsea. "'Make It Last'—Stretch That Conditioner!" Curly Nikki, Mar. 21, 2011, www.curlynikki.com/2013/06/stretch-that-conditioner.html. (Year: 2011).*
Bhattacharya, Stuti. "6 Conditioner Tips and Tricks for the Silkiest Hair Ever." iDiva, Feb. 16, 2018, www.idiva.com/beauty/hair/6-conditioner-tips-and-tricks-for-the-silkiest-hair-ever/17074561. Accessed Jun. 1, 2023. (Year: 2018).*
EWG. "What is Guar Hydroxypropyltrimonium Chloride." EWG. https://web.archive.org/web/20200929085144/https://www.ewg.org/skindeep/ingredients/702759-GUAR_HYDROXYPROPYLTRIMONIUM_CHLORIDE/ (Year: 2020).*
Stein, Richard. (Dec. 16, 2004 as evidenced by Wayback Machine). "Chapter 3: "Set Free—The Book About Hair"" Richard Stein Hair. https://www.richardsteinhair.com/chapter3.htm (Year: 2004).*
Morris, J. (2015, Oct. 29). "Is double shampooing the secret to perfect hair?" Allure. https://www.allure.com/story/double-shampoo-method. (Year: 2015).*
Database GNPD [Online], Mintel, Jun. 27, 2016, anonymous: "Conditioner," XP55659800, retrieved from www.gnpd.com, Database accession No. 4097969, abstract.

(Continued)

*Primary Examiner* — Frederick F Krass
*Assistant Examiner* — Lucy M Tien
(74) *Attorney, Agent, or Firm* — Dennemeyer & Associates LLC

(57) ABSTRACT

A hair conditioning composition that is silicone free is described. The composition includes a fatty acid ester, a cationic surfactant and optional high melting fatty compound, an optional organic acid, an optional cationic polymer, an optional zwitterionic compound and an optional antidandruff compound.

22 Claims, No Drawings

(56) References Cited

OTHER PUBLICATIONS

Database GNPD [Online], Mintel, May 13, 2009, anonymous: "Instant Nourishing Conditioner," XP55659807, retrieved from www.gnpd.com, Database accession No. 1103599, abstract.
Database GNPD [Online], Mintel, Aug. 1, 2014, anonymous: "Conditioner for Color Treated Hair," XP55660014, retrieved from www.gnpd.com, Database accession No. 2554073, abstract.
Database GNPD [Online], Mintel, Apr. 11, 2018, anonymous: "Mild Purifying Conditioner," XP55633608, retrieved from www.gnpd.com, Database accession No. 5583081, abstract.
International Search Report in connection to PCT/EP2019/079707 dated Feb. 3, 2020.
Written Opinion in connection to PCT/EP2019/079707 dated Feb. 3, 2020.
Office Action issued in Japan Patent Application in connection with Application No. 2021-523627 on May 24, 2022.
Response to Office Action and Official Receipt in connection to Japan Patent Application Application No. 2021-523627 filed on Aug. 19, 2022.
Decision of Rejection issued in Japan Patent Application in connection with Application No. 2021-523627 on Nov. 4, 2022.
Notice of Third-party Submission of Observations issued in Japan Patent Application in connection with Application No. 2021-523627 on Oct. 11, 2022.

\* cited by examiner

SILICON FREE HAIR CONDITIONING COMPOSITION

This application claims the benefit of priority to U.S. Provisional Applications No. 62/754,092, filed on Nov. 1, 2018, and U.S. Provisional Applications No. 62/757,821, filed on Nov. 9, 2018, which applications are incorporated by reference herein in its entirety.

FIELD OF THE INVENTION

The present invention relates to a composition for treating keratin fibers, in particular human hair, which greatly improves the conditioning properties and the luster and feel of such fibers without use of silicone compounds.

BACKGROUND OF THE INVENTION

Human hair becomes soiled due to its contact with the surrounding environment and from the sebum secreted by the scalp. The soiling of hair causes it to have a dirty feel and an unattractive appearance. The soiling of the hair necessitates shampooing with frequent regularity.

Shampooing cleans the hair by removing excess soil and sebum. However, shampooing can leave the hair in a wet, tangled, and generally unmanageable state. Once the hair dries, it is often left in a dry, rough, lusterless, or frizzy condition due to removal of the hair's natural oils and other natural conditioning and moisturizing components. The hair can further be left with increased levels of static upon drying, which can interfere with the combing and result in a condition commonly referred to as "fly-away hair", or contribute to an undesirable phenomenon of "split ends". Further, chemical treatments, such as perming, bleaching, or coloring hair, can also damage hair and leave it dry, rough, lusterless, and damaged.

A variety of approaches have been developed to condition the hair. A common method of providing conditioning benefits to the hair is through the use of conditioning agents such as cationic surfactants and high melting point fatty compounds, silicone compounds, and mixtures thereof.

Especially silicone compounds have been excessively used over the past decades to provide conditioners with enhanced benefits such as hair shine, softness, dry hair smoothness, hair strand alignment (e.g. minimize frizziness), and ease of combing.

However, consumers are becoming more aware of the safety of the ingredients used in their cosmetic products. In particular, the use of silicone and silicone-based products has drawn negative attention from the media. Silicone and its derivatives, though widely used in cosmetics for many years, are once again undergoing scrutiny for their safety as well as environmental impact. In view of this situation, silicone and its derivatives may fall out of favor with consumers, requiring formulators to find suitable substitutes if they are to continue providing high conditioning treatments for keratin fibers. Accordingly, there is a need for keratin fiber treatment which are free of silicone compounds.

SUMMARY OF THE INVENTION

The present invention can provide a highly effective conditioning composition, thus providing hair conditioning benefits such as hair shine, softness, dry hair smoothness, hair strand alignment (e.g., minimize frizziness), and ease of combing. Also, the present invention is effective for providing conditioning benefits to hair that is damaged by natural, environmental factors such as shampooing, as well as chemical hair treatments such as bleaching, coloring, or perming. The composition for conditioning hair may be applied to hair of any quality and/or origin including mammalian keratin fibers, especially human hair such as but not limited to human scalp hair.

The embodiments of the present invention are directed to a composition for conditioning hair that does not contain a silicone conditioning compound or a silicone compound of any kind. These embodiments are directed to a composition of an aqueous mixture of at least one fatty acid ester and at least one quaternary ammonium cationic surfactant that delivers the conditioning benefits described above. This composition may further include a high melting fatty compound which may be a fatty alcohol, fatty acid or derivative thereof, or combination thereof. The composition may further include an organic acid, a cationic polymer, a zwitterionic compound, a preservative and an antidandruff compound.

The concentrations of the ingredients of the compositional embodiments are determined to provide the benefits described above.

DETAILED DESCRIPTION

The present invention is directed to hair conditioning compositional embodiments that provide free flowing hair that is non-sticky, shiny, smooth, ease of combing, and has desirable tactile feel. The compositional embodiments are free from silicone ingredients.

Definitions

Unless defined otherwise, all technical and scientific terms used herein have the same meaning as commonly understood by a person of ordinary skill in the art.

As used in the specification and the appended claims, the singular forms "a," "an" and "the" include plural referents unless the context clearly dictates otherwise.

The term "may" in the context of this application means "is permitted to" or "is able to" and is a synonym for the term "can." The term "may" as used herein does not mean possibility or chance.

The term "at least one" means one and/or more than one of the item indicated and includes the single and multiples thereof. Multiples of the item indicated can be different species and/or variations of the item such as but not limited to situations when the item is a generic description covering more than one possibility. The term covers and includes a single example, specie or embodiment of the item indicated as well as multiples of the same, different or variations of the examples, species or embodiments of the item indicated. For example, at least one halogen includes a single halogen such as one of fluorine chlorine, bromine or iodine and includes multiples thereof such as any combination in any order of these halogens and multiples of any single halogen.

The molecular weight of a polymer or oligomer used according to the invention may be measured by a weight average molecular weight, and the distribution of molecules of different molecular weights of a polymer or oligomer used according to the invention is determined by its polydispersity index. Molecular weight is expressed as Daltons (Da) and kiloDaltons (kDa). The acronym wmw stands for weight average molecular weight Polydispersity is a unit-less number and indicates the breadth of the Gaussian curve plotted as the molecular weight of individual molecules (X axis) against the number of molecules at each molecular weight (Y-axis).

The term "about" is understood to mean±10 percent of the recited number, numbers or range of numbers.

The term "%" is synonymous with "wt %" and means the weight percentage of the amount of a component in the composition and is relative to the total weight of the composition. The weight percentage of a compound may also be expressed as a range of weight percentages such as about 2 wt % to about 20 wt %. This range includes each integer and each one-tenth of an integer between the two ends of the expressed range and is conditioned also by the term "about" discussed above.

The term "about 0 wt %" is understood to mean that no substance, compound or material to which zero (0) refers is present, up to a negligible but detectable amount is present, assuming that the detectability can be determined on a part per million basis.

The term "solvent" is understood to mean an organic liquid solvent such as ethyl acetate, methyl ethyl ketone, acetone, mono alcohols such as methanol, ethanol, propanol or butanol, or any other organic solvent having an STP (standard temperature and pressure) boiling point of 100° C. or lower and in which methacrylate monomers and oligomers and ethyl cellulose will dissolve.

In addition, where features or aspects of the invention are described in terms of Markush groups, those skilled in the art will recognize that the invention is also thereby described in terms of any individual member or subgroup of members of the Markush group. For example, if X is described as selected from the group consisting of methyl, ethyl or propyl, claims for X being methyl and claims for X being methyl and ethyl are fully described. Moreover, where features or aspects of the invention are described in terms of Markush groups, those skilled in the art will recognize that the invention is also thereby described in terms of any combination of individual members or subgroups of members of Markush groups. Thus, for example, if X is described as selected from the group consisting of bromine, chlorine, and iodine, and Y is described as selected from the group consisting of methyl, ethyl, and propyl, claims for X being bromine and Y being methyl are fully described.

If a value of a variable that is necessarily an integer, e.g., the number of carbon atoms in an alkyl group or the number of substituents on a ring, is described as a range, e.g., 0-4, what is meant is that the value can be any integer between 0 and 4 inclusive, i.e., 0, 1, 2, 3, or 4.

The term "substantially free" means that a substance characterized as being "substantially free" of a material contains little or none of that material. In quantitative terms, this term means that the substance contains at best zero weight percent of the material, and/or at worst contains no more than about 2 to 4 weight percent of the material, preferably no more than about 0.1 to 0.5 weight percent of the material, more preferably no more than about 0.01 to 0.1 weight percent of the material.

The Composition

The present invention is directed to a conditioning composition for treating hair to provide shine, softness, smoothness, strand alignment, free flow and lively hair. The composition for conditioning hair comprises i) one or more fatty acid esters, ii) one or more cationic surfactants and an aqueous carrier wherein the hair conditioning composition is substantially free of silicone compounds. The concentrations of the fatty acid ester and cationic surfactant respectively range from about 1% to about 20% and from about 0.1% to about 10%.

The composition further may comprise any one or more of a high melting point fatty alcohol or derivative thereof, a high melting fatty acid or derivative thereof, a cationic polymer, a zwitterionic compound and/or a anti-dandruff compound. The composition is formulated in an aqueous medium of water or a solution of water and a mono alcohol of 1 to 6 carbons, or a solution of water and a polyol of 2 to 6 carbons or a solution of water and a mixture of the monoalcohol and polyol.

The present invention is further directed to a method of using the conditioning composition.

Fatty Acid Ester

The conditioning composition of the present invention comprises a fatty acid ester which is included in the composition at a level by weight of from about 1 wt % to about 20 wt %, preferably from about 2.5 wt % to about 15 wt %, more preferably about 2.5 wt % to about 8 wt %, most preferably about 3.5 wt % to about 6.0 wt %, relative to the total weight of the composition.

Fatty acid esters useful herein include, for example, those corresponding to the general formula: according to the following formula $R^1CO_2R^2$ of the structure:

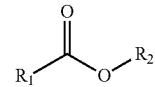

wherein R1 is a saturated or unsaturated, branched or linear alkyl moiety including 6 to 30 carbon atoms and R2 is saturated or unsaturated, branched or linear alkyl moiety including 7 to 29 carbon atoms.

Nonlimiting examples of such preferred fatty acid ester include: Hydrogenated Ethylhexyl Olivate with tradename Plantasens from Clariant, Hexyldecyl Stearate with tradename Eutanol® G 16 S from BASF, Octyl Stearate with tradename Cetiol 868 from BASF, Decyl Oleate with tradename Cetiol V from BASF, Stearyl Heptanoate with tradename Tegosoft SH from Evonik. Additional non-limiting examples of saturated fatty acids from which the esters can be formed include caprylic acid, capric acid, lauric acid, myristic acid, palmitic acid, stearic acid, arachidinic acid, behenic acid, lignoceric acid, cerotic acid and the homo derivatives thereof (one additional carbon). Non limiting examples of unsaturated fatty acid from which the esters can be formed include myristoleic acid, palmitoleic acid, sapienic acid, oleic acid, elaidic acid, vaccenic acid, linoleic acid, linoelaidic acid, alpha linolenic acid, arachidonic acid, eicosapentaenoic acid, erucic acid, docosahexaenoic acid. Mixtures of the saturated and unsaturated individual acids are also included as fatty acid mixtures from which the ester can be made. An example is olivic acid from olive oil which contains a mixture of oleic acid, linoleic acid palmitic acid, stearic acid and alpha linolenic acid. The esterifying alcohols include but are not limited to saturated alcohols such as ethylhexyl, octanol, pelargonic, decanol, undecyl, lauryl, tridecyl, nyristyl, pentadecyl, cetyl, palmitoleyl, heptadecyl, stearyl oleyl, nonadecyl, arachidyl, heneicosyl, behenyl, erucyhl, lignoceryl, ceryl alcohol. Unsaturated fatty alcohols include but are not limited to decenol, octenol, nonenol, undecenol, oleyl alcohol, cetenol, stearenol, linolenol, behenenol, and similar alcohols. Combinations of the fatty acids and fatty alcohols as esters produce examples of the fatty acid ester component of the hair conditioning composition embodiments of the invention.

Cationic Surfactant

The conditioning composition of the present invention comprises a cationic surfactant. The cationic surfactant is included in the composition at a level by weight of from about 0.1 wt % to about 10 wt %, preferably from about 0.1 wt % to about 8 wt %, more preferably about 0.5 wt % to about 5 wt %, most preferably about 0.5 wt % to about 3.5 wt %, relative to the total weight of the composition.

Cationic surfactants useful herein include, for example, those corresponding to the general formula:

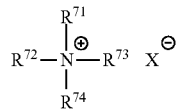

wherein at least one of R71, R72, R73 and R74 is selected from an aliphatic group of from about 8 to about 30 carbon atoms or an aromatic, alkoxy, polyoxyalkylene, alkylamido, hydroxyalkyl, aryl or alkylaryl group having up to about 22 carbon atoms, the remainder of $R^{71}$, $R^{72}$, $R^{73}$ and $R^{74}$ are independently selected from an aliphatic group of from about 1 to about 22 carbon atoms or an aromatic, alkoxy, polyoxyalkylene, alkylamido, hydroxyalkyl, aryl or alkylaryl group having up to about 22 carbon atoms; and X is a salt-forming anion such as those selected from halogen, (e.g. chloride, bromide), acetate, citrate, lactate, glycolate, phosphate, nitrate, sulfonate, sulfate, alkylsulfate, and alkyl sulfonate radicals. The aliphatic groups can contain, in addition to carbon and hydrogen atoms, ether, ester, or amido linkages and other groups such as amino groups. The longer chain aliphatic groups, (e.g., those of about 12 carbons, or higher), can be saturated, unsaturated, or branched. Preferred is when R71, R72, R73 and R74 are independently selected from C1 to about C22 alkyl. Nonlimiting examples of cationic surfactants useful in the present invention include the materials having the following CTFA designations: quaternium-8, quaternium-14, quaternium-18, quaternium-18 methosulfate, quaternium-24, and mixtures thereof.

Among the cationic surfactants of general formula above, preferred are those containing in the molecule at least one alkyl chain having at least 16 carbons. Nonlimiting examples of such preferred cationic surfactants include: behenyl trimethyl ammonium chloride available, for example, with tradename Genamine KDMP from Clariant, with tradename Incroquat Behenyl TMS-50 from Croda, and with tradename ECONOL TM22 from Sanyo Kasei; cetyl trimethyl ammonium chloride available, for example, with tradename CTAC 30KC from KCl, and with tradename CA-2350 from Nikko Chemicals; stearyl trimethyl ammonium chloride available from Parchem; olealkonium chloride available, for example, with tradename Incroquat™ TMS-50 from Croda; hydrogenated tallow alkyl trimethyl ammonium chloride, dialkyl (14-18) dimethyl ammonium chloride, ditallow alkyl dimethyl ammonium chloride, dihydrogenated tallow alkyl dimethyl ammonium chloride, distearyl dimethyl ammonium chloride, dicetyl dimethyl ammonium chloride, di(behenyl/arachidyl) dimethyl ammonium chloride, dibehenyl dimethyl ammonium chloride, stearyl dimethyl benzyl ammonium chloride, stearyl propyleneglycol phosphate dimethyl ammonium chloride, stearoyl amidopropyl dimethyl benzyl ammonium chloride, stearoyl amidopropyl dimethyl (myristylacetate) ammonium chloride, and N-(stearoyl colamino formyl methyl) pyridinium chloride.

Also preferred are hydrophilically substituted cationic surfactants in which at least one of the substituents contains one or more aromatic, ether, ester, amido, or amino moieties present as substituents or as linkages in the radical chain, wherein at least one of the R71-R74 radicals contain one or more hydrophilic moieties selected from alkoxy (preferably C1-C3 alkoxy), polyoxyalkylene (preferably C—C3 polyoxyalkylene), alkylamido, hydroxyalkyl, alkylester, and combinations thereof. Preferably, the hydrophilically substituted cationic conditioning surfactant contains from about 2 to about 10 nonionic hydrophile moieties located within the above stated ranges. Highly preferred hydrophilically substituted cationic surfactants include dialkylamido ethyl hydroxyethylmonium salt, dialkylamidoethyl dimonium salt, dialkyloyl ethyl hydroxyethylmonium salt, dialkyloyl ethyldimonium salt, and mixtures thereof; for example, commercially available under the following tradenames; VARISOFT 110, VARISOFT 222, VARIQUAT K1215 and VARIQUAT 638 from Evonik; MACKPRO KLP, MACKPRO WLW, MACKPRO MLP, MACKPRO NSP, MACKPRO NLW, MACKPRO WWP, MACKPRO NLP, MACKPRO SLP from Solvay; ETHOQUAD 18/25, ETHOQUAD O/12PG, ETHOQUAD C/25, ETHOQUAD S/25, and ETHODUOQUAD from Akzo; DEHYQUART SP from BASF; and ATLAS G265 from Croda. Babassuamidopropalkonium Chloride available from Croda under the tradename Incroquat BA-85 is also preferably used in the composition.

Amines are suitable as cationic surfactants. Primary, secondary, and tertiary fatty amines are useful. Particularly useful are tertiary amido amines having an alkyl group of from about 12 to about 22 carbons. Exemplary tertiary amido amines include: stearamidopropyldimethylamine, stearamidopropyldiethylamine, stearamidoethyldiethylamine, stearamidoethyldimethylamine, palmitamidopropyldimethyl amine, palmitamidopropyldiethylamine, palmitamidoethyldiethylamine, palmitamidoethyldimethylamine, behenamidopropyldimethylamine, ehenamidopropyldiethylamine, behenamidoethyldiethylamine, behenamidoethyldimethylamine, arachnidamidopropyldimethylamine, arachidamidopropyldiethylamine, arachidamidoethyldiethylamine, arachidamidoethyldimethylamine, diethylaminoethylstearamide. Also useful are dimethylstearamine, dimethylsoyamine, soyamine, myristylamine, tridecylamine, ethylstearylamine, N-tallowpropane diamine, ethoxylated (with 5 moles of ethylene oxide) stearylamine, dihydroxyethylstearylamine, and arachidylbehenylamine. Useful amines in the present invention are disclosed in U.S. Pat. No. 4,275,055.

High Melting Point Fatty Compound

The hair conditioning composition of the present invention may further contain a high melting point fatty compound. The high melting point fatty compound may be a fatty alcohol or derivative thereof or a fatty acid or derivative thereof. This high melting fatty compound has the general formula R—X, wherein R is an aliphatic (e.g. fatty chain) and X is a functional group (e.g. alcohol, acid, or derivative). Suitable high melting point fatty compounds useful herein have a melting point of at least about 25° C., preferably about at least 30° C. The aliphatic group R may be a linear or branched saturated or unsaturated carbon chain of 8 to 30 carbons, preferably 12 to 20 carbons. The fatty compound is selected from the group consisting of fatty alcohols, fatty acids, fatty alcohol derivatives, fatty acid derivatives, and mixtures thereof. The fatty alcohol derivatives may be mono alcohols, polyols, polyethers, polyepoxys, esterified fatty alcohols, esterified polyols, esterified polyethers and mixtures thereof It is understood by the artisan that the compounds disclosed in this section of the specification can in some instances fall into more than one classification, (e.g. some fatty alcohol derivatives can also be classified as fatty acid derivatives). However, a given classification is not intended to be a limitation on that particular compound, but is done so for convenience of classification and nomenclature.

Further, it is understood by the artisan that, depending on the number and position of double bonds and length and position of the branches, certain compounds having certain required carbon atoms may have a melting point of less than 25° C. Such compounds of low melting point are not included in this feature of the high melting point fatty compound. However, such fatty compounds of such lower melting points may be included as additional components described below as long as the content of such lower melting point fatty compounds does not ameliorate or minimize the beneficial effects of the high melting fatty compounds. Nonlimiting examples of the high melting point compounds are found in International Cosmetic Ingredient Dictionary, Fifth Edition, 1993, and CTFA Cosmetic Ingredient Handbook, Second Edition, 1992.

The high melting point fatty compound can be included in the composition at a level of from about 0.1 wt % to about 20 wt %, preferably from about 1 wt % to about 10 wt %, still more preferably from about 2 wt % to about 9 wt %, relative to the total weight of the composition. It is preferred that the high melting point fatty compound is included at a level so that the mole ratio of the cationic surfactant to the high melting fatty compound is from about 1:1 to about 1:8.

The fatty alcohols useful herein are those having from about 8 to about 30 carbon atoms, preferably from about 16 to about 22 carbon atoms. These fatty alcohols are saturated and can be straight or branched chain alcohols. Nonlimiting examples of fatty alcohols include cetyl alcohol, stearyl alcohol, behenyl alcohol, and mixtures thereof.

The fatty acids useful herein are those having from about 10 to about 30 carbon atoms, preferably from about 12 to about 25 carbon atoms, and more preferably from about 16 to about 22 carbon atoms. These fatty acids are saturated or unsaturated and can be straight or branched chain acids. Also included are diacids, triacids, and other multiple acids which meet the requirements herein. Also included herein are salts of these fatty acids. Nonlimiting examples of fatty acids include lauric acid, cetylic acid, palmitic acid, stearic acid, behenic acid, sebacic acid, arachidic acid, behenic acid, oleic acid, palmitolic acid, elaidic acid, linoleic acid, linolenic acid, arachidonic acid or eicosapentaenoic acid or mixtures thereof.

The fatty alcohol derivatives and fatty acid derivatives useful herein include alkyl ethers of fatty alcohols, alkoxylated fatty alcohols, alkyl ethers of alkoxylated fatty alcohols, fatty acid esters of compounds having esterifiable hydroxy groups, hydroxy-substituted fatty acids, and mixtures thereof. Nonlimiting examples of fatty alcohol derivatives and fatty acid derivatives include materials such as methyl stearyl ether; the ceteth series of compounds such as ceteth-1 through ceteth-45, which are ethylene glycol ethers of cetyl alcohol, wherein the numeric designation indicates the number of ethylene glycol moieties present; the steareth series of compounds such as steareth-1 through steareth-10, which are ethylene glycol ethers of steareth alcohol, wherein the numeric designation indicates the number of ethylene glycol moieties present; ceteareth 1 through ceteareth-10, which are the ethylene glycol ethers of ceteareth alcohol, (e.g. a mixture of fatty alcohols containing predominantly cetyl and stearyl alcohol, wherein the numeric designation indicates the number of ethylene glycol moieties present); C1-C30 alkyl ethers of the ceteth, steareth, and ceteareth compounds just described; polyoxyethylene ethers of behenyl alcohol; ethyl stearate, cetyl stearate, cetyl palmitate, stearyl stearate, myristyl myristate, polyoxyethylene cetyl ether stearate, polyoxyethylene stearyl ether stearate, polyoxyethylene lauryl ether stearate, ethyleneglycol monostearate, polyoxyethylene monostearate, polyoxyethylene distearate, propyleneglycol monostearate, propyleneglycol distearate, trimethylolpropane distearate, sorbitan stearate, polyglyceryl stearate, glyceryl monostearate, glyceryl distearate, glyceryl tristearate, and mixtures thereof.

High melting point fatty compounds of a single compound of high purity are preferred. Single compounds of pure fatty alcohols selected from the group consisting of pure cetyl alcohol, stearyl alcohol, and behenyl alcohol are highly preferred. By "pure" herein, what is meant is that the compound has a purity of at least about 90%, preferably at least about 95%. These single compounds of high purity provide good rinsability from the hair when the consumer rinses off the composition.

Commercially available high melting point fatty compounds useful herein include: cetyl alcohol, stearyl alcohol, and behenyl alcohol available from Parchen, various fatty acids having tradenames NEO-FAT available from Akzo, HYSTRENE available from PMC Group.

Organic Acid

The hair conditioning composition of the present invention may further comprise an organic acid selected from the group consisting of L-glutamic acid, lactic acid, malic acid, succinic acid, acetic acid, fumaric acid, L-glutamic acid, tartaric acid, citric acid, and mixtures thereof and similar mild to moderate organic acids. An inorganic acid such as aqueous hydrochloric acid or similar pharmacologically acceptable inorganic acid may be used but is not preferred. Preferably the acid is an organic acid having a moderate acidity, more preferable the acid is L-glutamic acid, lactic acid, citric acid, and mixtures thereof.

Use of Organic Acid

The organic acids described herein are primarily present to partially neutralize the amines described herein including the cationic polymers, the cationic surfactants, the zwitterionic compounds and any other amine compound included in the composition for conditioning hair. The organic acid is used at a concentration and ratio to at least partially neutralize the amines. The molar equivalent ratio of the amine to the acid (molar equivalent of amine to molar equivalent of acid) of from about 1:0.3 to about 1:2, more preferably from about 1:0.4 to about 1:1.3. In other words, from partial neutralization of the amine to full neutralization and excess of acid.

Cationic Polymer

The cationic polymer useful herein has an average molecular weight of at least about 5,000, typically from about 10,000 to about 10 million, preferably from about 100,000 to about 2 million. The cationic polymer differs from the cationic surfactant because of its polymeric character and the number of nitrogen groups in the molecule. The cationic polymer has repeating units of olefinic monomer residues linked together by free radical addition or carbohydrate (polysaccharide or cellulose) residues while the cationic surfactant has aliphatic groups as substituents of the nitrogen. The cationic polymer contains multiple nitrogen groups as amines or quaternary groups or has multiple phosphonium groups while the cationic surfactant contains a single nitrogen group as an amine or quaternary group.

Suitable cationic polymers include, for example, copolymers of vinyl monomers having cationic amine or quaternary ammonium functionalities with optional water soluble spacer monomers or non-polar olefinic spacer monomers. The water soluble spacer monomers include such polar monomers as acrylamide, methacrylamide, alkyl and dialkyl acrylamides, alkyl and dialkyl methacrylamides, alkyl acrylate, alkyl methacrylate, vinyl caprolactone, and vinyl pyrrolidone. Other suitable spacer monomers include vinyl esters, vinyl alcohol (made by hydrolysis of polyvinyl acetate), maleic anhydride, propylene glycol, and ethylene glycol. The non-polar oldrinic spacer monomers include ethylene, propylene, butene, isoprene, styrene and similar olefin monomers. Other suitable cationic polymers useful herein include, for example, cationic celluloses, cationic starches, and cationic guar gums wherein the cationic groups are ammonium or phosphonium groups.

The cationic polymer can be included in the hair conditioning composition of the present invention at a level of from about 0.001 wt % to about 10 wt %, preferably from about 0.005 wt % to about 5 wt %, more preferably about 0.01 wt % to about 5 wt % most preferably from about 0.1 wt % to about 5 wt % relative to the total weight of the composition.

Zwitterionic Compound

The embodiments of the composition of the invention may also include a zwitterionic compound, such as a betaine alkyl glycine, a glyceryl fatty acid ester, an N-fatty acyl, an N-aminoalkyl, N-hydroxyalkylamino acid wherein the amino acid is glycine, alanine, valine, leucine, isoleucine or phenyl alanine, and any combination of any of these more specific embodiments.

In yet another embodiment, a useful class of amine compounds is the class of quaternized phosphate esters, as depicted in general structural formula:

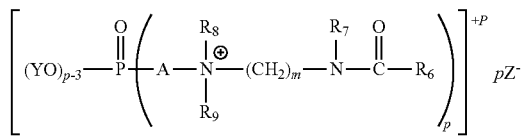

Wherein R6 is an aryl, an alkaryl, a saturated or unsaturated alkyl group, or a saturated or unsaturated hydroxyalkyl group, wherein the alkyl or hydroxyalkyl group includes about seven to about 21 carbon atoms; R7 is hydrogen, or an alkyl or a hydroxyalkyl group including one to about six carbon atoms; R8 and R9, independently, are an alkyl or a hydroxyalkyl group including one to about six carbon atoms; A is a residue of a glycol or a triol having two to about four carbon atoms, such as the residue of propylene glycol (—OCH2CH(OH)CH2-); Z is an anion selected from the group consisting of chloride, bromide, methosulfate, ethosulfate, and combinations thereof; m is a numeral from one to about 10; Y is selected from the group consisting of hydrogen, an alkyl group, a hydroxyalkyl group, and an aryl group, either substituted or unsubstituted, and wherein the alkyl or the hydroxyalkyl group includes one to about 22 carbon atoms; and p is a number from 1 to 3. To achieve the full advantage of the present invention, the quaternized phosphate ester is a quaternized phosphate diester that includes the alkyl moiety of an essential fatty acid, like linoleic acid, arachidonic acid or ricinoleic acid, as the R6 substituent of the compound. For example, the quaternized phosphate ester of general structural formula below that includes the alkyl moiety of an essential fatty acid as the R6 substituent and wherein the number p is 2.

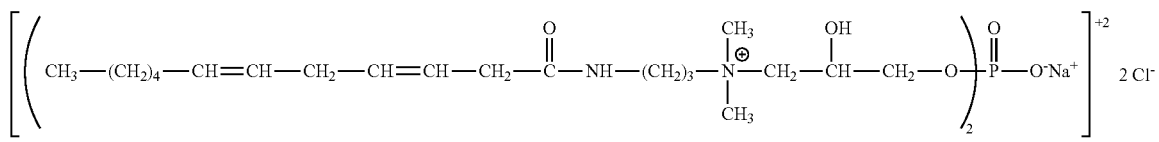

compound, a sultaine compound, or a diamino carboxylic acid compound. These compounds are zwitterionic derivatives of amine/quaternary ammonium compounds, amino acids or hydroxyl amino acids. Preferred quaternary ammonium organic compounds are the cationic compounds having only a positive charged group, such as but not limited to quaternary ammonium compounds. The zwitterionic compounds include an anionic group or anionic salt as a neutralizing group as well as the cationic quaternary group.

More specific embodiments of the zwitterionic compound include a quaternary ammonium compound, a fatty acyl aminoalkyl betaine, a fatty acyl betaine, a fatty acyl aminopropyl sultaine, a fatty acyl sultaine, a N-fatty acyl amino- The zwitterionic compound can be included in the hair conditioning composition at a concentration ranging from about 0.001 wt % to about 6 wt %, preferably about 0.01 wt % to about 4 wt %, more preferably about 0.01 wt % to about 3 wt % and most preferably about 0.01 wt % to about 1.5 to 2 wt % relative to the total weight of the composition.

Aqueous Carrier

The conditioning composition of the present invention comprises an aqueous carrier. The level and species of the carrier are selected according to the compatibility with other components and other desired characteristics of the product.

The carrier useful in the present invention includes water and water solutions of lower alkyl alcohols and polyhydric alcohols. The lower alkyl alcohols useful herein are monohydric alcohols having 1 to 6 carbons, preferably ethanol and isopropanol. The polyhydric alcohols useful herein include propylene glycol, hexylene glycol, glycerin, and propane diol.

Preferably, the aqueous carrier is substantially water. Deionized water is preferably used. Water from natural sources including mineral cations can also be used, depending on the desired characteristic of the product. Generally, the compositions of the present invention comprise from about 20 wt % to about 95 wt %, preferably from about 30 wt % to about 92 wt %, and more preferably from about 50 wt % to about 90 wt % of an aqueous carrier relative to the total weight of the composition.

Preservatives

Preservatives including parabens, ethanol, phenoxyethanol, benzoic acid, sodium benzoate, benzyl alcohol, isothiazolinones, DMDM hydantoin, diazolidinyl urea, sorbic acid, potassium sorbate, levulinic acid, and similar cosmetically acceptable preservatives. The preservative may be included at concentrations of from about 0.01 wt % to about 2 wt %, preferably about 0.1 wt % to about 0.8 wt % relative to the total weight of the composition.

Additional Components

The composition of the present invention may include other additional components, which may be selected by the artisan according to the desired characteristics of the final product and which are suitable for rendering the composition more cosmetically or aesthetically acceptable or to provide them with additional usage benefits. Such other additional components generally are used individually at levels of from about 0.001% to about 10%, preferably up to about 5% by weight of the composition.

One of the additional components is a fatty acid polyol ester compound or fatty acid polyepoxy ester compound or fatty acid complex mono or poly alcohol ester. These fatty acid compounds are similar to the high melting fatty acid derivative described above but do not have the high melting temperature. They may be liquid to highly viscous at ambient temperature and may be present at a concentration of from about 0.1 wt % to about 15 wt %, preferably about 0.1 wt % to about 10 wt %, more preferably about 0.1 wt % to about 5 wt %, especially more preferably about 0.2 wt % to about 5 wt %, most preferably about 0.5 wt % to about 5 wt % relative to the total weight of the composition.

A wide variety of other additional components can be formulated into the present compositions. These include: other conditioning agents such as vitamin E, panthenol, panthenyl ethyl ether, hydrolysed keratin, proteins, plant extracts, and nutrients, emollients such as PPG-3 myristyl ether, Trimethyl pentanol hydroxyethyl ether, moisturizers such as Sodium lactate, Sodium PCA, Glycine, Fructose, Urea, Niacinamide, Inositol, hair-fixative polymers such as amphoteric fixative polymers, cationic fixative polymers, anionic fixative polymers, nonionic fixative polymers, preservatives such as benzyl alcohol, methyl paraben, propyl paraben and phenoxyethanol, pH adjusting agents, such as citric acid, sodium citrate, succinic acid, phosphoric acid, sodium hydroxide, sodium carbonate; salts, in general, such as potassium acetate and sodium chloride, coloring agents, such as any of the FD&C or D&C dyes, hair oxidizing (bleaching) agents, such as hydrogen peroxide, perborate and persulfate salts, hair reducing agents such as the thioglycolates, perfumes, sequestering agents, such as disodium ethylenediamine tetra-acetate; ultraviolet and infrared screening and absorbing agents such as octyl salicylate; and antidandruff agents such as zinc pyrithione and climbazole sulfur, sublimed sulfur, ketoconazole, salicylic acid, coal tar extract, selenium sulfide, ciclopirox or clobetasol; thickeners/rheology modifiers such as nonionic homopolymers and copolymers containing ethylenically unsaturated monomers of the ester and/or amide type; homo- and copolymers of vinylpyrrolidone, and polysaccharides, polyacrylamides, methyl methacrylate/ethylene glycol dimethacrylate copolymers, butyl methacrylate/methyl methacrylate copolymers, and polymethyl methacrylates, glucans, modified or unmodified starches (i.e. hydroxypropyl starch phosphate), amylose, amylopectin, glycogen, dextrans, celluloses and derivatives thereof (methylcelluloses, hydroxyalkylcelluloses, ethylhydroxyethylcelluloses), mannans, xylans, lignins, arabans, galactans, galacturonans, chitin, chitosans, glucoronoxylans, arabinoxylans, xyloglucans, glucomannans, pectic acids and pectins, arabinogalactans, carrageenans, agars, gums arabic, gums Tragacanth, Ghatti gums, Karaya gums, carob gums, galactomannans and mixtures thereof.

It has been surprisingly discovered that the claimed combination of one or more surfactants with a fatty acid ester and an optional fatty alcohol delivers an unexpected high hair conditioning effect which are typically only achievable with the use of Silicones.

EXAMPLES

Embodiments of Silicone-Free Conditioner Compositions According to the Invention Example 1

| Raw Material | Amount | Property |
| --- | --- | --- |
| Behentrimonium Chloride | 3.2 g (2.5-4 g) | Cationic surfactant |
| Cetearyl Alcohol | 3.0 g (2.0-3.5 g) | High melting fatty compound |
| Hydrogenated Ethyl Hexyl Olivate | 5.5 g (3-6 g) | Fatty acid ester |
| Hydroxypropyl Starch Phosphate | 2.0 g (1.5-2.5 g) | Emulsifier/cationic polymer |
| Citric Acid | 0.1 g (0.05-0.3 g) | Organic acid |
| Phenoxyethanol | 0.9 g (0.5-1.5 g) | preservative |
| Perfume | 0.5 g (0.3-1 g) | |
| Water | to 100 g | Aqueous solvent |

Example 2

| Raw Material | Amount |
| --- | --- |
| Behentrimonium Chloride | 2.3 g (2-2.5 g) |
| Stearyl Alcohol | 4.2 g (4-4.5 g) |
| Cetyl Alcohol | 1.7 g (1.5-2 g) |
| Hexyldecyl Stearate | 5.5 g (3-6) g |
| Benzyl Alcohol | 0.5 g (0.3-0.7 g) |
| Phenoxyethanol | 0.5 g (0.3-0.7 g) |
| Perfume | 0.5 g (0.3-0.8 g) |
| Water | to 100 g |

Example 3

| Raw Material | Amount |
| --- | --- |
| Behentrimonium Chloride | 2.25 g |
| Cetearyl Alcohol | 6.5 g |
| Hydrogenated Ethyl Hexyl Olivate | 3.7 g |
| Benzyl Alcohol | 0.5 g |
| Phenoxyethanol | 0.5 g |
| Perfume | 0.5 g |
| Water | to 100 g |

Example 4

| Raw Material | Amount |
| --- | --- |
| Cetrimonium Chloride | 0.65 g |
| Cetearyl Alcohol | 4.5 g |
| Octyl Stearate or decyl oleate | 2.5 g |
| Benzyl Alcohol | 0.5 g |
| Phenoxyethanol | 0.5 g |
| Perfume | 0.5 g |
| Water | to 100 g |

Example 5

| Raw Material | Amount |
| --- | --- |
| Behenamidopropyl Dimethylamine | 2.3 g |
| Cetyl Alcohol | 1.85 g |
| Stearyl Alcohol | 4.5 g |
| Hydrogenated Ethyl Hexyl Olivate | 3.7 g |
| Linoleamidopropyl PG-Dimonium Chloride Phosphate | 1.2 g |
| Benzyl Alcohol | 0.5 g |
| Phenoxyethanol | 0.5 g |
| Perfume | 0.6 g |
| Water | to 100 g |

Example 6

| Raw Material | Amount |
| --- | --- |
| Behenamidopropyl Dimethylamine | 2.3 g |
| Cetyl Alcohol | 1.85 g |
| Stearyl Alcohol | 4.5 g |
| Hydrogenated Ethyl Hexyl Olivate | 5.5 g |
| Benzyl Alcohol | 0.5 g |
| Phenoxyethanol | 0.5 g |
| Perfume | 0.6 g |
| Water | to 100 g |

Example 7

| Raw Material | Amount |
| --- | --- |
| Stearamidopropyl Dimethylamine | 0.12 g |
| Ditallow Dimethylammonium Chloride | 1.0 g |
| Stearyl Alcohol | 0.75 g |
| Cetyl Alcohol | 1.1 g |
| Hydrogenated Ethyl Hexyl Olivate | 3.0 g |
| Hydroxyethyl Cellulose | 0.5 g |
| Benzyl Alcohol | 0.5 g |
| Phenoxyethanol | 0.5 g |
| Perfume | 0.6 g |
| Water | to 100 g |

Half Head Examination of Conditioner Examples

The ability of the foregoing conditioner examples to condition the hair is examined by a procedure involving the steps of shampooing and conditioning. The procedure is conducted by shampooing the hair with shampoo that contains no conditioner and subsequently towel-drying the hair. The towel-dried hair is then parted in the middle into two sections from brow to neck. One of the sections is treated with the present invention (example 1), the other section is treated with the reference conditioner.

Evaluation Criteria for Half Head Examination

Rinse Ability:
Evaluation of rinse ability is determined by assessing whether a conditioner is easier or more difficult to wash out of the hair after application time. Evaluation is conducted visually by noting no visible conditioner in the hair which can be seen by lack of foam.

Combability:
Combability of the hair is assessed by placing an aluminum comb parallel to the middle parting and running it through the hair to the shoulder. The comb must remain at a 90° angle throughout and remain in contact with the scalp throughout combing to avoid varying comb angles. The amount of resistance/effort needed during combing is the basis for evaluating the product as easier to comb/more difficult to comb. This test can be carried out on wet hair and on dry hair as well. The evaluation is conducted manually and is compared to the combability of the hair with reference conditioner Dry Feel:
When the hair is completely dry, the evaluating stylist assesses the dry feel of the hair. This is assessed by running the hair from root to end between the thumb and middle and index fingers, while simultaneously applying light pressure; or alternatively, by running lightly outspread fingers through the hair from root to end. If the hair runs easily through the fingers, this is referred to as a smooth feel; if the hair is impeded from running easily through the fingers, this is referred to as a coarse feel.

Hair Shine:
Hair shine is evaluated by looking at the reflection of light on the hair under standard conditions (natural daylight or a daylight lamp). From a distance of 0.5 m, and with slight head movements by the model, the light reflection or shine is evaluated as more/less.

Frizz:
Hair Frizz is evaluated optically—on straight hair styles via assessing if short strands sticking up at the part and throughout the hair length that "project away from the main body of hair", and on curly hair via assessing how much strands of wavy or curly hair do not align with others to form a defined wave or curl. The less hair sticking up on straight hair and the more defined/less unruly curls or waves are observed, the less frizzy the hair is.

Examination Results

Half head examination 1 was carried out with 5 test persons, the numbers indicated how many test persons were judged for each criterion.

| Criterion | Example 1 better than reference conditioner | Example 1 equal than reference conditioner | Example 1 worse than reference conditioner |
| --- | --- | --- | --- |
| Rinseability | 2 | 1 | 2 |
| Wet Combability | 3 | 1 | 1 |
| Dry Feel* | 4 | 1 | — |
| Hair Shine | 1 | 3 | 1 |
| Hair Frizz* | 4 | 1 | — |

*statistically significant difference (p > 0.9)

Reference conditioner: Example 3, but Hexyldecyl Stearate replaced by 1% Bis-Aminopropyl Dimethicone to deliver high wet and dry conditioning.

Half head examination 2 was carried out with 3 test persons, the numbers indicated for how many test persons each criterion was judged how:

| Criterion | Example 1 better than reference conditioner | Example 1 equal than reference conditioner | Example 1 worse than reference conditioner |
| --- | --- | --- | --- |
| Rinseability | 1 | 1 | 1 |
| Wet Combability | 1 | — | 2 |
| Dry Feel | 2 | 1 | — |
| Hair Shine | — | 3 | — |
| Hair Frizz | — | 2 | 1 |

To note:
the differences are statistically not significant.

Reference conditioner: Example 2, but Hydrogenated Ethyl Hexyl Olivate replaced by 1% Abil Quat 3272 (INCI: Quaternium-80, quaternized Amino Silicone) and 2% Dow Corning 939 Cationic Emulsion (INCI: Amodimethicone).

The results of half head examination 1 indicates clearly that the conditioner according to the present invention leads to comparable rinseability, wet combability and hair shine, but even better dry hair feel and frizz reduction, despite the fact that the reference conditioner contains an highly effective Silicone based conditioning agent (Bis-Aminopropyl Dimethicone).

Half head examination 2 results also indicates that the conditioner according to the present invention delivers basically the same conditioning performance vs. a conditioner containing highly effective, functionalized Silicones (Quaternium-80 and Amodimethicone).

Net—the silicone free conditioner according to the present invention has a surprisingly strong hair conditioning effect, comparable to Silicone-containing conditioners which are the benchmark for high conditioning effectiveness since decades.

What is claimed is:

1. A composition for hair conditioning, consisting of:
    at least one fatty acid ester wherein the fatty acid ester has the formula $R^1CO_2R^2$ wherein $R^1$ is a saturated or unsaturated linear alkyl moiety including 6 to 30 carbon atoms and $R^2$ is a saturated, linear alkyl moiety including 7 to 29 carbon atoms, and the concentration of the at least one fatty acid ester is about 1 wt % to 20 wt % relative to the total weight of the composition;
    one cationic surfactant consisting of a quaternary ammonium compound of the formula $R^3R^4NR^5R^6 X$ wherein at least one of $R^3$, $R^4$, $R^5$ and $R^6$ is selected from an aliphatic group of 8 to 30 carbons, aromatic, alkoxyalkyl, polyoxyalkylene, amidoalkyl, hydroxyalkyl, aryl or alkylaryl of up to 22 carbons, and the remainder of $R^3$, $R^4$, $R^5$ and $R^6$ are each independently selected from methyl, ethyl, phenyl or benzyl, X is a salt forming anion and the concentration of the quaternary ammonium cationic surfactant comprises about 0.1 wt % to about 10 wt % relative to the total weight of the composition;
    one or more of a high melting point compound consisting of a saturated fatty alcohol of from 14 to 30 carbon atoms, having a melting point of at least 25° C., and a concentration of from about 0.1 wt % to about 20 wt % relative to the total weight of the composition;
    one or more of a cationic polymer comprising an olefinic polymer, a cellulosic polymer, guar gum or starch, each having amine or quaternary ammonium groups or phosphonium groups at a concentration of from about 0.1 wt % to about 20 wt % relative to the total weight of the composition;
    an organic acid selected from the group consisting of L-glutamic acid, lactic acid, malic acid, succinic acid, acetic acid, fumaric acid, tartaric acid, citric acid and a mixture thereof, the concentration of organic acid being determined relative to the concentration of cationic polymer present, the molar equivalent being about 1:0.3 to about 1:2 of cationic polymer to acid;
    an aqueous medium comprising water or water and a mono alcohol of 1 to 6 carbons or a polyol of 2 to 6 carbons;
    an optional ingredient comprising one or more of a preservative, a fatty acid polyester compound, a fatty acid polyepoxy ester compound, a fatty acid complex mono or poly alcohol ester, vitamin E, panthenol, panthenyl ethyl ether, hydrolyzed keratin, plant extract, emollient, moisturizer, pH adjusting agent, salt, coloring agent, perfume, sequestering agent, IR screen, antidandruff agent, thickener, rheology modifier, homo- or copolymer of vinylpyrrolidone, polysaccharide, polyacrylamide, methyl methacrylate/ethylene glycol dimethacrylate copolymer, butyl methacrylate/methyl methacrylate copolymer, polymethyl methacrylate, glucan, modified or unmodified starch, hydroxypropyl starch phosphate, amylose, amylopectin, glycogen, dextran, cellulose, methylcellulose, hydroxyalkylcellulose, ethylhydroxyethylcellulose, mannan, xylan, lignin, araban, galactan, galacturonan, chitin, chitosan, glucoronoxylan, arabinoxylan, xyloglucas, glucomannan, pectic acid, pectin, arabinogalactan, carrageenan, agar, gum arabic, gum Tragacanth, Ghatti gum, Karaya gum, carob gum, galactomannan and any combination thereof, and,
    wherein, the composition for hair conditioning is free of a silicone compound of any kind.

2. The composition of claim 1 wherein the $R^1$ group of the fatty acid ester is saturated.

3. The composition of claim 1 wherein the cationic polymer is an olefinic polymer with amine or quaternary ammonium groups.

4. The composition of claim 3 wherein the olefinic polymer includes water soluble spacer monomeric units comprising one or more monomeric residues of (meth)

acrylamide, alkyl (meth)acrylate, vinyl alkanoate, vinyl alcohol, and vinyl pyrrolidone.

5. The composition of claim 1 wherein the concentrations of the at least one fatty acid ester and the cationic surfactant respectively are about 2.5 wt % to about 15 wt % and about 0.1 wt % to about 8 wt % relative to the total weight of the composition.

6. The composition of claim 1 wherein the concentrations of the at least one fatty acid ester and the cationic surfactant respectively are about 2.5 wt % to about 8 wt % and about 0.5 wt % to about 5 wt % relative to the total weight of the composition.

7. The composition of claim 1 wherein the concentrations of the at least one fatty acid ester and the cationic surfactant respectively are about 3.5 wt % to about 6 wt % and about 0.5 wt % to about 3.5 wt % relative to the total weight of the composition.

8. The composition of claim 1 wherein the cationic polymer has a concentration of up to about 5 wt % relative to the total weight of the composition.

9. The composition of claim 1 wherein the at least one fatty acid ester is hydrogenated ethyl hexyl olivate, hexadecyl stearate, octyl stearate, stearyl heptanoate, stearyl laurate, cetyl caprate, stearyl caprate, lauryl palmitate or any combination thereof.

10. The composition of claim 9 wherein the at least one fatty acid ester is hydrogenated ethyl hexyl olivate, hexadecyl stearate, octyl stearate or stearyl heptanoate or any combination thereof.

11. The composition of claim 1 wherein the cationic surfactant is behentrimonium chloride, cetrimonium chloride, dibehenyl dimethyl ammonium chloride, ditallow dimethylammonium chloride, or stearoyl amidopropyl dimethyl benzyl ammonium chloride.

12. The composition of claim 1 wherein the fatty alcohol is cetyl alcohol, stearyl alcohol, lauryl alcohol, decyl alcohol, cetearyl alcohol or a combination thereof.

13. The composition of claim 1 wherein the cationic polymer is a (meth)acrylamide-vinylamine copolymer, methyl (meth)acrylate-vinylamine copolymer or dialkyl-(2-hydroxypropyl) aminoethyl cellulose, linoleamidopropyl PG-dimonium chloride phosphate, hydroxyethylcellulose or any combination thereof.

14. The composition of claim 1 wherein the optional ingredient comprises at least the antidandruff compound at a concentration of from about 0.01 wt % to about 0.8 wt % relative to the total weight of the composition.

15. The composition of claim 14 wherein the antidandruff compound is zinc pyrithione, climbazole, sulfur, sublimed sulfur, ketoconazole, salicylic acid, coal tar extract, selenium sulfide, ciclopirox or clobetasol.

16. A method for conditioning hair comprising applying the composition of claim 1 to a person's scalp hair.

17. The method of claim 16 wherein the hair is wet or damp.

18. The method of claim 16 wherein the hair has been shampooed, rinsed with water and dried to dampness before applying the conditioning composition.

19. The method of claim 16 wherein the hair is rinsed with water and dried to dampness before applying the conditioning composition.

20. The method of claim 16 wherein the hair is rinsed with water after application of the conditioning composition and dried.

21. The method of claim 20 wherein the dried hair had been dried with a flow of warm air.

22. The method of claim 16 wherein the composition is diluted with water before applying to the hair.

* * * * *